(12) United States Patent
Kuwana et al.

(10) Patent No.: US 10,364,199 B2
(45) Date of Patent: Jul. 30, 2019

(54) PROPANE PRODUCTION METHOD AND PROPANE PRODUCTION APPARATUS

(71) Applicant: SUMITOMO SEIKA CHEMICALS CO., LTD., Hyogo (JP)

(72) Inventors: Akihiro Kuwana, Hyogo (JP); Junichi Kawakami, Hyogo (JP); Shuji Tsuno, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 15/523,910

(22) PCT Filed: Jan. 21, 2016

(86) PCT No.: PCT/JP2016/051737
§ 371 (c)(1),
(2) Date: May 2, 2017

(87) PCT Pub. No.: WO2016/121622
PCT Pub. Date: Aug. 4, 2016

(65) Prior Publication Data
US 2017/0349506 A1  Dec. 7, 2017

(30) Foreign Application Priority Data

Jan. 29, 2015  (JP) .................. 2015-016126

(51) Int. Cl.
*C07C 5/03* (2006.01)
*C07C 7/12* (2006.01)
(Continued)

(52) U.S. Cl.
CPC ............. *C07C 5/03* (2013.01); *C07C 7/04* (2013.01); *C07C 7/09* (2013.01); *C07C 7/13* (2013.01); *C07C 7/163* (2013.01); *C07C 9/08* (2013.01)

(58) Field of Classification Search
CPC ..... C07C 5/03; C07C 9/08; C07C 7/04; C07C 7/13; C07C 7/163
See application file for complete search history.

(56) References Cited

U.S. PATENT DOCUMENTS 3,509,226 A * 4/1970 Eng .......................... C07C 5/03
585/258
2003/0177903 A1  9/2003 Reyes et al.
(Continued)

FOREIGN PATENT DOCUMENTS

JP  2002-356448 A  12/2002
JP  2006-508020 A  3/2006
(Continued)

OTHER PUBLICATIONS

JP 2013-129606_English (Year: 2013).*
(Continued)

*Primary Examiner* — Youngsul Jeong
(74) *Attorney, Agent, or Firm* — Harness Dickey & Pierce P.L.C.

(57) ABSTRACT

A propane production method includes a hydrogenation reaction step of hydrogenation-reacting crude propylene and hydrogen in a presence of a catalyst to obtain gaseous crude propane containing impurities; and an impurity removal step of removing the impurities contained in the gaseous crude propane obtained in the hydrogenation reaction step to obtain purified propane. The impurity removal step includes an adsorptive removal stage of adsorbing and removing water, ethane and propylene contained as impurities in the gaseous crude propane by adsorption treatment in which the gaseous crude propane is brought into contact with an adsorbent, and a separation removal stage of separating and removing hydrogen, oxygen, nitrogen and methane contained as impurities in the crude propane after the adsorption (Continued)

treatment by partial condensation or distillation of crude propane after the adsorption treatment in the adsorptive removal stage.

4 Claims, 3 Drawing Sheets

(51) Int. Cl.
    *C07C 9/08*     (2006.01)
    *C07C 7/04*     (2006.01)
    *C07C 7/13*     (2006.01)
    *C07C 7/163*     (2006.01)
    *C07C 7/09*     (2006.01)

(56) References Cited

U.S. PATENT DOCUMENTS

| | | |
|---|---|---|
| 2007/0261995 A1 | 11/2007 | Corma Canos et al. |
| 2014/0343341 A1 | 11/2014 | Kawakami et al. |

FOREIGN PATENT DOCUMENTS

| | | | |
|---|---|---|---|
| JP | 2008-513194 A | 5/2008 | |
| JP | 2012-025729 A | 2/2012 | |
| JP | 2012-153632 A | 8/2012 | |
| JP | 2013-063951 | 4/2013 | |
| JP | 2013-129606 | * 7/2013 | ............... C07C 7/12 |
| JP | 2013-129606 A | 7/2013 | |
| JP | 2014-080399 A | 5/2014 | |
| JP | 2014-084285 A | 5/2014 | |
| JP | 2014-091733 A | 5/2014 | |
| TW | 201420564 A | 6/2014 | |

OTHER PUBLICATIONS

Bremaud et al. (Hydrogenation of propene on sulfide catalysts-H-D isotopic study, Fuel Chemistry Division Preprints, 2003, 48(1), 129, Source: https://web.anl.gov/PCS/acsfuel/.../Files/48_1_ New%20Orleans_03-03_0416.pdf). (Year: 2003).*

Eisele et al. (Propene, 2005 Wiley-VCH Verlag GmbH & Co.) (Year: 2005).*

International Preliminary Report on Patentability dated Aug. 11, 2017 issued in International Patent Application No. PCT/JP2016/051737.

International Search Report dated Apr. 5, 2016 issued in PCT/JP2016/051737.

Taiwanese Office Action dated Apr. 19, 2019 issued in Taiwanese Patent Application No. 105102553 (with English summary), 5 pages.

* cited by examiner

PROPANE PRODUCTION METHOD AND PROPANE PRODUCTION APPARATUS

PRIORITY STATEMENT

This patent application is a U.S. national stage filing under 35 U.S.C. § 371 of International Application No. PCT/JP2016/051737, which has an international filing date of 21 Jan. 2016 and claims priority under 35 U.S.C. § 119 to JP 2015-016126, filed on 29 Jan. 2015. The entire disclosure of each of the above applications is incorporated herein by reference.

TECHNICAL FIELD

The present invention relates to a propane production method and a propane production apparatus.

BACKGROUND ART

Propane is used in the field of semiconductor electronic materials, such as materials for SiC which is a next generation power device material, and is used in hydrogen diluted propane gas and propane pure gas. For such application, propane is required to have higher purity.

In a raw material gas containing propane as a main component used as a raw material of high purity propane, for example, ethane, propylene, isobutane and normal butane are contained at high concentration as impurities. Examples of a method of purifying propane from the raw material gas include methods such as distillation, membrane separation, adsorption separation, absorption separation and the like.

Patent Literature 1 describes a method of separating propylene and propane by a distillation method. For example, in the case of separating propylene and propane by the distillation method as in the technique described in Patent Literature 1, since boiling points thereof are close to each other (boiling point difference is 4.9° C.), it is required to repeat the distillation in multiple stages for separation thereof. Accordingly, it is required to set up large-scale equipment and precise distillation conditions, which is a huge barrier to putting the equipment into practical use.

Patent Literature 1 describes a method of adsorbing and separating isobutane and normal butane, and propane using activated carbon and adsorbing and separating ethane and propylene, and propane using molecular sieve activated carbon. In the technique described in Patent Literature 2, although propane of high purity can be obtained without performing complicated operations such as distillation, when isobutane and normal butane and propane are adsorbed and separated using the activated carbon, there is a problem that the amount of propane adsorbed on the activated carbon is large and the yield of propane is poor.

As a method for solving such a problem, Patent Literature 3 describes a method of generating propane by bringing propylene and hydrogen into contact with each other to perform a hydrogenation reaction.

CITATION LIST

Patent Literature

Patent Literature 1: Japanese Unexamined Patent Publication JP-A 2002-356448
Patent Literature 2: Japanese Unexamined Patent Publication JP-A 2013-129606
Patent Literature 3: United States Patent Publication U.S. Pat. No. 3,509,226

SUMMARY OF INVENTION

Technical Problem

In a propane production method described in Patent Literature 3, since propane is generated from propylene by a hydrogenation reaction, propane can be efficiently produced without complicated operations such as distillation.

However, in the propane production method described in Patent Literature 3, in the hydrogenation reaction accompanied by heat generation to generate propane from propylene, when the reaction temperature is excessively high, the impurities such as methane and ethane are generated. As a result, propane of high purity cannot be obtained.

An object of the invention is to provide a propane production method and a propane production apparatus that can efficiently obtain propane of high purity with high yield.

Solution to Problem

The invention provides a propane production method, comprising:
a hydrogenation reaction step of performing a hydrogenation reaction of crude propylene and hydrogen in a presence of a catalyst to obtain gaseous crude propane containing impurities; and
an impurity removal step of removing the impurities contained in the gaseous crude propane obtained in the hydrogenation reaction step to obtain purified propane.

In the propane production method according to the invention, the impurities include at least one of hydrogen, oxygen, nitrogen, water, methane, ethane, and propylene.

In the propane production method according to the invention, the impurity removal step includes an adsorptive removal step of adsorbing and removing water, ethane and propylene contained as impurities in the gaseous crude propane by adsorption treatment in which the gaseous crude propane is brought into contact with an adsorbent, and a separation removal step of separating and removing hydrogen, oxygen, nitrogen and methane contained as impurities in crude propane after the adsorption treatment by partial condensation or distillation of the crude propane after the adsorption treatment in the adsorptive removal step.

In the propane production method according to the invention, the adsorbent is molecular sieve zeolite and molecular sieve activated carbon.

In the propane production method according to the invention, the molecular sieve zeolite and the molecular sieve activated carbon are porous bodies having pores with a pore diameter of 4 angstroms. "Angstrom (Å)" is $10^{-10}$ m in length and 4 angstroms corresponds to 0.4 nm (nanometer).

In the propane production method according to the invention, the adsorption treatment in the adsorptive removal step is performed under conditions of temperature of 5 to 50° C. and pressure of 0.1 to 0.5 MPaG. The above "G" indicates that the pressure is based on the gauge pressure, and the same applies to the following pressure indication.

The invention provides a propane production apparatus, comprising;
a hydrogenation reaction section that performs a hydrogenation reaction of crude propylene and hydrogen in a presence of a catalyst to obtain gaseous crude propane containing impurities; and an impurity removing section that removes the impurities contained in the gaseous crude propane obtained in the hydrogenation reaction section to obtain purified propane.

Advantageous Effects of Invention

According to the invention, the propane production method includes the hydrogenation reaction step and the impurity removal step. In the hydrogenation reaction step, the crude propylene and hydrogen are subjected to the hydrogenation reaction in the presence of the catalyst, so that the gaseous crude propane containing impurities is obtained.

In the case of generating propane by the hydrogenation reaction, since when the reaction temperature of the hydrogenation reaction accompanied by heat generation is excessively high, the impurities such as methane and ethane are generated, and therefore complicated temperature control of controlling the reaction temperature with high accuracy is required to obtain propane of high purity. A method for producing propane of high purity by using a hydrogenation reaction in which such a reaction temperature is controlled with high accuracy is less than an efficient method.

Therefore, the propane production method of the invention does not control the reaction temperature of the hydrogenation reaction with high accuracy, but, in the impurity removal step, removes the impurities (main impurities include at least one of hydrogen, oxygen, nitrogen, water, methane, ethane, and propylene) contained in the crude propane obtained in the hydrogenation reaction step to obtain the purified propane. Accordingly, the propane production method of the invention can efficiently obtain the purified propane of high purity with high yield.

According to the invention, the impurity removal step has the adsorptive removal step and the separation removal step. In the adsorptive removal step, the water, ethane, and propylene contained as impurities in the crude propane are adsorbed and removed by an adsorption treatment in which the crude propane is brought into contact with the adsorbent (molecular sieve zeolite and molecular sieve activated carbon which are porous bodies having pores with pore diameters of 4 angstroms). The adsorption treatment in the adsorptive removal step is performed under the conditions of temperature of 5 to 50° C. and pressure of 0.1 to 0.5 MPaG.

In the separation removal step, hydrogen, oxygen, nitrogen and methane contained as the impurities in the crude propane after an adsorption treatment are separated and removed by the partial condensation or the distillation of the crude propane after the adsorption treatment in the adsorptive removal step. In this manner, at least one of hydrogen, oxygen, nitrogen, water, methane, ethane, and propylene contained as impurities in the crude propane obtained in the hydrogenation reaction step can be efficiently removed, and propane of high purity can be obtained.

According to the invention, the propane production apparatus includes the hydrogenation reaction section and the impurity removal section. In the hydrogenation reaction section, the crude propylene and hydrogen are subjected to the hydrogenation reaction in the presence of the catalyst, so that the gaseous crude propane containing impurities is obtained. The impurity removal section removes the impurities (main impurities include at least one of hydrogen, oxygen, nitrogen, water, methane, ethane, and propylene) contained in the crude propane obtained in the hydrogenation reaction section to obtain the purified propane. Accordingly, the propane production apparatus of the invention can efficiently obtain the purified propane of high purity with high yield.

BRIEF DESCRIPTION OF DRAWINGS

Other and further objects, features, and advantages of the invention will be more explicit from the following detailed description taken with reference to the drawings wherein.

DESCRIPTION OF EMBODIMENTS

Figure 1:
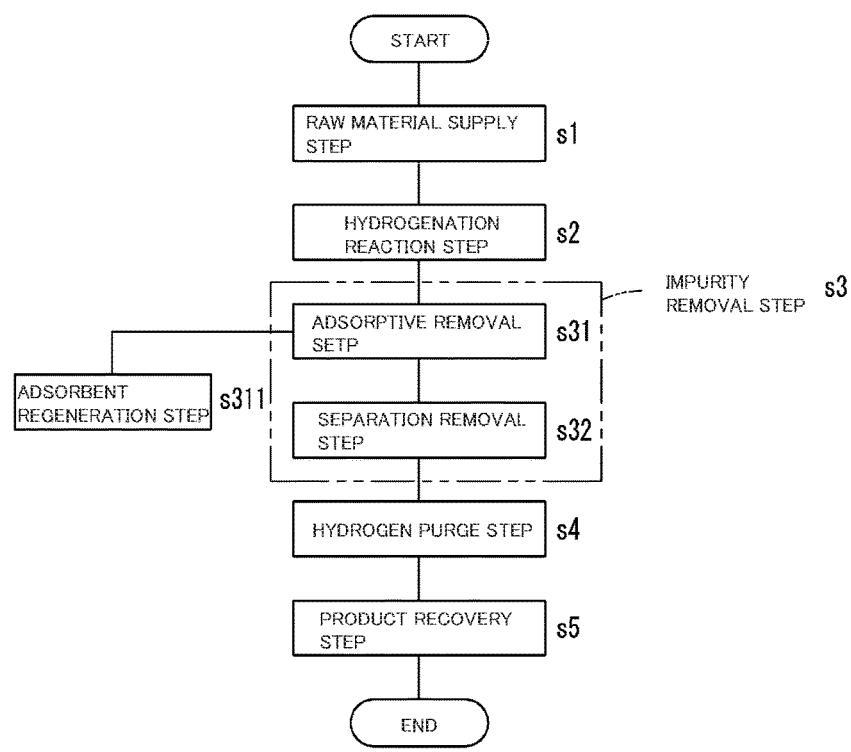
FIG. 1 is a diagram illustrating steps of a propane production method according to an embodiment of the invention.

FIG. 1 is a diagram illustrating steps of a propane production method according to an embodiment of the invention. The propane production method of the embodiment includes a raw material supply step s1, a hydrogenation reaction step s2, and an impurity removal step s3 having an adsorptive removal step s31 and a separation removal step s32, a hydrogen purge step s4, and a product recovery step s5. In addition, the propane production method of the embodiment further includes an adsorbent regeneration step s311 for performing regeneration treatment of an adsorbent used in the adsorptive removal step s31.

Figure 2:
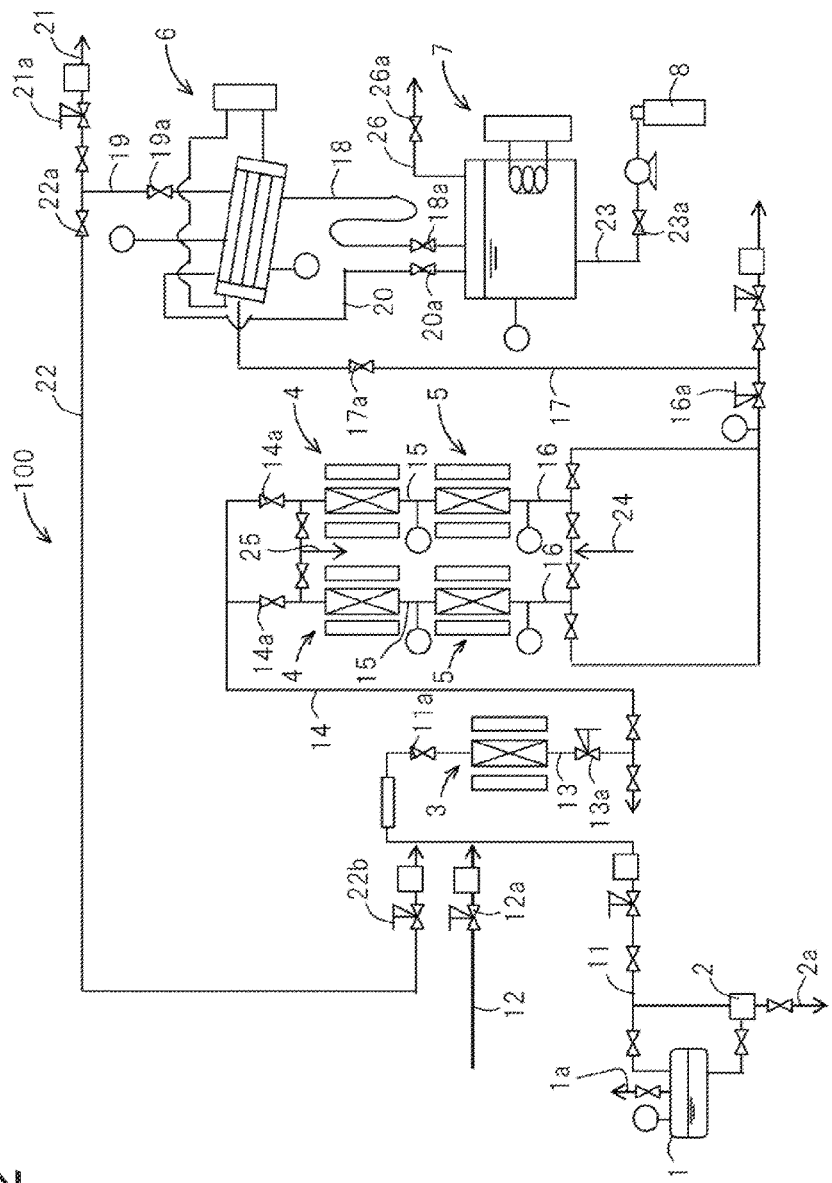
FIG. 2 is a diagram illustrating a configuration of a propane production apparatus 100 according to a first embodiment of the invention.

FIG. 2 is a diagram illustrating a configuration of a propane production apparatus 100 according to a first embodiment of the invention. The propane production apparatus 100 of the embodiment includes a raw material propylene storage tank 1; a vaporizer 2; a hydrogenation reaction tower 3 functioning as a hydrogenation reaction section; a first adsorption tower 4, a second adsorption tower 5 and a partial condenser 6 that function as an impurity removal section; a recovery vessel 7; and a filling cylinder 8. This propane production apparatus 100 is an apparatus for performing the propane production method according to the embodiment, in which the raw material propylene storage tank 1 and the vaporizer 2 perform the raw material supply step s1, the hydrogenation reaction tower 3 performs the hydrogenation reaction step s2, the first adsorption tower 4 and the second adsorption tower 5 perform the adsorptive removal step s31 and the adsorbent regeneration step s311 of the impurity removal step s3, the partial condenser 6 performs the separation removal step s32 and the hydrogen purge step s4, and the recovery vessel 7 and the filling cylinder 8 perform the product recovery step s5.

The raw material propylene storage tank 1 is a tank for storing crude propylene serving as a reaction raw material of a hydrogenation reaction in the hydrogenation reaction tower 3 described later. As illustrated in Table 1, the crude propylene contains methane, ethane, propane, nitrogen, and oxygen as main impurities.

TABLE 1

| | Analysis value (concentration: vol.ppm) | | | | | | | | | | |
|---|---|---|---|---|---|---|---|---|---|---|---|
| | Methane | Acetylene | Ethylene | Ethane | Propylene | Propane | i-butane | n-butane | Pentane | Nitrogen | Oxygen |
| Propane | 5 | <1 | <1 | 7500 | 200 | — | 290 | 10 | <1 | 4000 | 100 |
| Propylene | 20 | <1 | <1 | 100 | — | 3800 | <1 | <1 | <1 | 10000 | 200 |

In addition, as illustrated in Table 1, the crude propylene has a low impurity content concentration in isobutane (i-butane) and normal butane (n-butane), as compared with crude propane which can be generally available. As described above, since the crude propylene has the low impurity content concentration in isobutane and normal butane, by producing propane using the crude propylene, it is not required to adsorb and remove isobutane and normal butane by an adsorption treatment using activated carbon as in the technique described in Patent Literature 2.

In this embodiment, the crude propylene having the impurity content concentration of isobutane, normal butane, and pentane respectively of less than 1.0 vol·ppm is used as raw material propylene. In addition, the purity of crude propylene is 95 mol % or more, and preferably 99 mol % or more.

The raw material propylene storage tank 1 stores liquid crude propylene so that a gaseous phase is formed in a head space thereof. A tank purge flow path pipe 1a is disposed in an upper portion of the raw material propylene storage tank 1. Nitrogen and oxygen contained in the liquid crude propylene stored in the raw material propylene storage tank 1 can be removed via the tank purge flow path pipe 1a.

In addition, a raw material supply flow path pipe 11 is disposed between the raw material propylene storage tank 1 and the hydrogenation reaction tower 3 described later. When the crude propylene is caused to flow out from the raw material propylene storage tank 1, gaseous crude propylene may be flowed out from the gaseous phase of the raw material propylene storage tank 1, or the liquid crude propylene may be flowed out from a liquid phase of the raw material propylene storage tank 1.

In a case where the liquid crude propylene is flowed out from the liquid phase of the raw material propylene storage tank 1, the liquid crude propylene is vaporized in the vaporizer 2 and supplied to the hydrogenation reaction tower 3 as the gaseous crude propylene. The vaporizer 2 may vaporize the entire liquid crude propylene flowed out from the liquid phase of the raw material propylene storage tank 1, or may vaporize a part of the liquid crude propylene flowed out from the liquid phase of the raw material propylene storage tank 1. In a case of vaporizing a part of the liquid crude propylene flowed out from the liquid phase of the raw material propylene storage tank 1, the vaporizer 2 vaporizes a part of the liquid crude propylene at a vaporization rate at which 85% to 98% by volume of the entire liquid crude propylene vaporizes. In this manner, for example, in a case where the crude propylene contains isobutane and normal butane as impurities, these impurities can be removed as liquid components via a vaporizer purge flow path pipe 2a.

The gaseous crude propylene flowed out from the gaseous phase of the raw material propylene storage tank 1, or the gaseous crude propylene that is flowed out from the liquid phase of the raw material propylene storage tank 1 and then vaporized in the vaporizer 2, flows through the raw material supply flow path pipe 11, and flows in the hydrogenation reaction tower 3 in a state where a flow path on-off valve 11a for opening and closing the flow path of the raw material supply flow path pipe 11 is opened.

In the raw material supply flow path pipe 11, a hydrogen introduction flow path pipe 12 is connected between the raw material propylene storage tank 1 and the hydrogenation reaction tower 3. The gaseous crude propylene flowing in the raw material supply flow path pipe 11 flows through the hydrogen introduction flow path pipe 12, and is mixed with hydrogen flowing in the raw material supply flow path pipe 11, in a state where a flow path on-off valve 12a for opening and closing the flow path of the hydrogen introduction flow path pipe 12 is opened. In this way, in the raw material supply flow path pipe 11, a mixed gas in which the crude propylene and the hydrogen are mixed flows through the raw material supply flow path pipe 11, and is supplied to the hydrogenation reaction tower 3.

A mixing ratio of the mixed gas obtained by mixing the crude propylene and hydrogen supplied to the hydrogenation reaction tower 3 is crude propylene/hydrogen=1/0.8 to 1/100, preferably crude propylene/hydrogen=1/1.1 to 1/10 in terms of molar ratio. In a case where the molar ratio of hydrogen to crude propylene is less than 0.8, propylene is not sufficiently hydrogenated to propane. When the molar ratio of hydrogen to crude propylene exceeds 100, a large amount of unreacted hydrogen remains in the produced propane, and thus it is difficult to separate and remove this hydrogen.

In the hydrogenation reaction tower 3, the crude propylene and hydrogen are subjected to a hydrogenation reaction in a presence of a catalyst, so that gaseous crude propane containing impurities is obtained. The hydrogenation reaction tower 3 has a hollow interior space, and the interior space thereof is filled with the catalyst. In addition, to the hydrogenation reaction tower 3, a temperature adjustment device for maintaining an interior of the hydrogenation reaction tower 3 at a desired temperature is attached. In the hydrogenation reaction tower 3, the crude propane is generated by bringing the crude propylene and hydrogen into contact with each other to be subjected to the hydrogenation reaction in the presence of the catalyst.

Although the catalyst filled in the hydrogenation reaction tower 3 is not particularly limited as long as the catalyst is a reduction catalyst, for example, the catalyst is preferably a catalyst containing at least one selected from palladium (Pd), rhodium (Rh), platinum (Pt), ruthenium (Ru), and nickel (Ni), and is particularly preferably a catalyst containing palladium (Pd). The hydrogenation reaction of propane is performed in the presence of such a catalyst so that the efficiency of the hydrogenation reaction can be improved, and the productivity of propane can be improved.

In a state where alumina ball, ceramic ball or the like are mixed with the catalyst, these may be filled in the hydrogenation reaction tower 3. In this manner, since heat generation accompanying the hydrogenation reaction can be suppressed in the hydrogenation reaction tower 3, the reaction temperature can be maintained constantly.

In addition, a space velocity SV of the mixed gas in which the crude propylene and hydrogen are mixed in the hydrogenation reaction tower 3 is, for example, 10 to 50000/hour, preferably 100 to 1000/hour. In a case where the space velocity SV is less than 10/hour, the amount of catalyst used in the hydrogenation reaction increases and the cost increases. When the space velocity SV exceeds 50000/hour, there is a possibility that sufficient hydrogenation reaction may not be performed.

In addition, the temperature in the hydrogenation reaction tower 3 is, for example, 0 to 700° C., and preferably 50 to 200° C. When the temperature exceeds 700° C., equipment cost for stabilizing the temperature is required, and there is further a possibility that decomposition of propylene at a higher concentration may occur.

In addition, the pressure in the hydrogenation reaction tower 3 is, for example, 0.0 to 1.0 MPaG (gauge pressure), and is preferably 0.0 to 0.5 MPaG. When the pressure exceeds 1.0 MPaG, although the hydrogenation reaction is promoted, a large amount of reaction heat is generated, and the reaction heat becomes an obstacle for stabilizing the reaction temperature. Furthermore, when the temperature is 25° C. or less under the pressure of 1.0 MPaG or more, propylene serving as the raw material and the generated propane are liquefied, so that it becomes difficult to control the reaction. In addition, when the pressure is less than 0.0 MPaG, the hydrogenation reaction is unlikely to progress.

In addition, when carbon monoxide is present in the catalyst used in the hydrogenation reaction, it is widely known that catalyst degradation occurs. In a case where a large amount of carbon monoxide is contained, the catalyst can be repeatedly used by regularly passing hydrogen gas or the like through the catalyst under high temperature to regenerate the catalyst. In a case where the concentration of carbon monoxide in the catalyst is extremely high, the carbon monoxide is removed using a generally available carbon monoxide adsorbent, and thereafter the catalyst may be used in the hydrogenation reaction.

The crude propane obtained by the hydrogenation reaction in the hydrogenation reaction tower 3 contains at least one of hydrogen, oxygen, nitrogen, water, methane, ethane, and propylene as main impurities. Hydrogen and propylene in the crude propane are those remained unreacted. Methane and ethane in the crude propane are those contained in the crude propylene, ethane generated by hydrogenation of ethylene and acetylene in the crude propylene, and methane and ethane generated in the decomposition reaction by heat generation of the hydrogenation reaction. The nitrogen and oxygen in the crude propane are those contained in crude propylene. The water in the crude propane is one generated by the reaction of the oxygen and hydrogen.

In the crude propane obtained by the hydrogenation reaction in the hydrogenation reaction tower 3, the impurity content concentration is, for example, 4.7 to 10.0 vol. % of hydrogen, 0 to 10 vol·ppm of oxygen, 50 to 500 vol·ppm of nitrogen, 1 to 50 vol·ppm of water, 1 to 50 vol·ppm of methane, 10 to 200 vol·ppm of ethane, and 0 to 100 vol·ppm of propylene. Oxygen reacts with hydrogen so that most of oxygen becomes water, and propylene becomes "0" when the hydrogenation reaction proceeds completely.

A crude propane outflow flow path pipe 13 is connected to the bottom portion of the hydrogenation reaction tower 3, and in a state where a flow path on-off valve 13a for opening and closing the flow path of the crude propane outflow flow path pipe 13 is opened, the gaseous crude propane obtained by the hydrogenation reaction flows through the crude propane outflow flow path pipe 13. A crude propane supply flow path pipe 14 is connected to the crude propane outflow flow path pipe 13, and the crude propane supply flow path pipe 14 is connected to the first adsorption tower 4. The crude propane having flowed through the crude propane outflow flow path pipe 13 flows through the crude propane supply flow path pipe 14 and is supplied to the first adsorption tower 4 in a state where a flow path on-off valve 14a for opening and closing the flow path of the crude propane supply flow path pipe 14 is opened. In addition, the second adsorption tower 5 is connected in series to the first adsorption tower 4 via a flow path pipe 15.

By the adsorption treatment in which the gaseous crude propane flowed out from the hydrogenation reaction tower 3 is brought into contact with the adsorbent, the first adsorption tower 4 and the second adsorption tower 5 adsorb and remove water, ethane and propylene contained as impurities in the crude propane.

The first adsorption tower 4 and the second adsorption tower 5 have a hollow interior space, and the interior space thereof is filled with the adsorbent. In addition, in the first adsorption tower 4 and the second adsorption tower 5, a temperature adjustment device for maintaining an interior of each adsorption tower at a desired temperature is attached.

The adsorbents filled in the first adsorption tower 4 and the second adsorption tower 5 are molecular sieve zeolite and molecular sieve activated carbon. The molecular sieve zeolite and the molecular sieve activated carbon are porous bodies having pores with uniform pore diameters, and each component in the crude propane is separated by a difference in molecular shape. The molecular sieve zeolite has high adsorption ability to water, and the molecular sieve activated carbon has high adsorption ability to ethane and propylene. The forms of the molecular sieve zeolite and the molecular sieve activated carbon are not particularly limited, and can be a granular shape or a pelletized shape, for example.

In addition, the molecular sieve zeolite and the molecular sieve activated carbon are preferably porous bodies having pores with a pore diameter of 4 angstroms, from the viewpoint of superior adsorption selectivity of adsorbing water, ethane and propylene as impurities without adsorbing propane.

In addition, it is preferable that the molecular sieve activated carbon is filled in the first adsorption tower 4 where the adsorption treatment in the former step is performed, and the molecular sieve zeolite is filled in the second adsorption tower 5 where the adsorption treatment in the latter step is performed.

In addition, the space velocity SV of the crude propane in the first adsorption tower 4 and the second adsorption tower 5 is, for example, 1 to 1000/hour, preferably 10 to 200/hour. In a case where the space velocity SV is less than 1/hour, the sizes of the first adsorption tower 4 and the second adsorption tower 5 are increased, and when the space velocity SV exceeds 1000/hour, the impurities are unlikely to be adsorbed by the adsorbent, and the length of adsorption zone increases. Therefore, there is a possibility that the usable time of the first adsorption tower 4 and the second adsorption tower 5 may be shortened.

In addition, the temperature in the first adsorption tower 4 and the second adsorption tower 5 is, for example, 5 to 50° C. When the temperature is lower than 5° C., there is a possibility that propane may liquefy depending on the pressure of the adsorption tower. When the temperature exceeds 50° C., the impurities adsorbed by the adsorbent are desorbed and the adsorption amount remarkably decreases. The temperatures in the first adsorption tower 4 and the second adsorption tower 5 are selected in the above range where propane is not liquefied, and the adsorption treatment time in the lower range increases in the above range.

In addition, the pressures in the first adsorption tower 4 and the second adsorption tower 5 are, for example, 0.1 to 0.5 MPaG (gauge pressure), and preferably 0.1 to 0.3 MPaG.

In addition, in the embodiment, each of the first adsorption tower 4 and the second adsorption tower 5 has a structure in which two adsorption towers are connected in parallel, for example, while adsorption treatment of the crude propane is performed by one first adsorption tower 4 and one second adsorption tower 5, it is possible to perform the regeneration treatment of the adsorbent filled in the used other first adsorption tower 4 and the used other second adsorption tower 5 so that the adsorption treatment can be performed again in the other first adsorption tower 4 and the other second adsorption tower 5.

The regeneration treatment of the adsorbent in the first adsorption tower 4 and the second adsorption tower 5 is performed by introducing a regeneration gas formed of an inert gas such as helium or argon to the first adsorption tower 4 and the second adsorption tower 5 via a regeneration gas supply flow path pipe 24 in a state where the temperatures in the first adsorption tower 4 and the second adsorption tower 5 are maintained at a predetermined temperature, and discharging the regeneration gas from the first adsorption tower 4 and the second adsorption tower 5 via a regeneration gas discharge flow path pipe 25.

The temperatures of the first adsorption tower 4 and the second adsorption tower 5 during the regeneration treatment of the adsorbent are preferably, for example, 200° C. to 300° C., and more preferably approximately 250° C. When the treatment temperature is lower than 200° C., the time required for the regeneration treatment of the adsorbent increases, and when the treatment temperature exceeds 300° C., the energy cost increases and there is a possibility that pulverization of the molecular sieve activated carbon may proceed.

When the concentration of each impurity component contained in the regeneration gas discharged from the first adsorption tower 4 and the second adsorption tower 5 via the regeneration gas discharge flow path pipe 25 is set to 50 vol·ppm or less, the adsorption capacity can be restored to 90% or more of the initial adsorption capacity of the molecular sieve activated carbon. Since the molecular sieve zeolite is likely to regenerate in comparison with the molecular sieve activated carbon, the regeneration is completed without problems when the regeneration is managed at the end point of the molecular sieve activated carbon. Since the time required for the regeneration treatment of the adsorbent varies depending on the flow rate of the regeneration gas, the adsorption amount of impurities, and the temperature in the adsorption tower, the time may be experimentally obtained.

A primary purified propane outflow flow path pipe 16 is connected to the bottom portion of the second adsorption tower 5, and in a state where a flow path on-off valve 16a for opening and closing the flow path of the primary purified propane outflow flow path pipe 16 is opened, the gaseous primary purified propane after the adsorption treatment flows through the primary purified propane outflow flow path pipe 16. A primary purified propane supply flow path pipe 17 is connected to the primary purified propane outflow flow path pipe 16, and the primary purified propane supply flow path pipe 17 is connected to the partial condenser 6. The primary purified propane having flowed through the primary purified propane outflow flow path pipe 16 flows through the primary purified propane supply flow path pipe 17 and is supplied to the partial condenser 6, in a state where a flow path on-off valve 17a for opening and closing the flow path of the primary purified propane supply flow path pipe 17 is opened.

The primary purified propane after the adsorption treatment in the first adsorption tower 4 and the second adsorption tower 5 is subjected to partial condensation so that the partial condenser 6 separates and removes hydrogen, oxygen, nitrogen and methane contained as impurities in the primary purified propane.

As the partial condenser 6, a multitubular heat exchanger, a double tube heat exchanger, a glass lining heat exchanger, a coil type heat exchanger, a helical type heat exchanger, a plate type heat exchanger, a trombone type heat exchanger, an impermeable graphite heat exchanger, or the like can be used.

As the material of the partial condenser 6, cast iron, stainless steel (SUS 304, SUS 316, SUS 316L, etc.), or the like can be preferably used. In addition, glass materials such as glass, heat-resistant glass and quartz glass can be preferably used, and a material coated with these materials on the metal surface, for example, a glass lining material can be used for the partial condenser 6.

In addition, the setting condition in the partial condenser 6 is not particularly limited as long as it is a condition for liquefying a part of propane in the primary purified propane. The temperature of the partial condenser 6 may be lower by approximately 1 to 3° C. than that of the recovery vessel 7 described later, for example, it is preferable to set the temperature of the partial condensation at −35° C. to 15° C. In a case where the temperature of the partial condensation is less than −35° C., a special cryogen for lowering the temperature is required, which is not preferable because the energy cost for cooling the cryogen increases. In addition, in a case where the temperature of the partial condensation exceeds 15° C., the pressure of the gaseous phase component increases, which is not preferable because equipment of pressure resistance is required. The temperature of the partial condensation in the partial condenser 6 is maintained at a predetermined temperature by using a refrigerant circulator.

In addition, the pressure in the partial condenser 6 is preferably, for example, 0.05 to 0.3 MPaG. By the partial condensation operation in the partial condenser 6, a part of the gaseous primary purified propane is liquefied by the partial condensation to be a liquid phase component, and a non-liquefied portion remains as a gas to be a gaseous phase component. A gaseous phase component outflow flow path pipe 19, a gaseous phase component discharge flow path pipe 21, and a liquid phase component outflow flow path pipe 18 are connected to the partial condenser 6.

A gaseous phase component supply flow path pipe 22 is connected to the gaseous phase component outflow flow path pipe 19, and in a state where a flow path on-off valve 19a for opening and closing the flow path of the gaseous phase component outflow flow path pipe 19 and flow path on-off valves 22a and 22b for opening and closing the flow path of the gaseous phase component supply flow path pipe 22 are opened, the gaseous phase component flowed out from the partial condenser 6 flows through the gaseous phase component outflow flow path pipe 19 and the gaseous phase component supply flow path pipe 22 and is supplied into the hydrogenation reaction tower 3 as a recycle material.

The impurity gaseous phase component containing hydrogen, oxygen and methane separated into the gaseous phase by the partial condensation using the partial condenser 6 flows through the gaseous phase component discharge flow path pipe 21, and is discharged to the outside, in a state where a flow path on-off valve 21a for opening and closing the flow path of the gaseous phase component discharge flow path pipe 21 is opened.

The purified propane of high purity (purity of 99.999 vol. % or more) separated into the liquid phase by the partial condensation using the partial condenser 6 flows through the liquid phase component outflow flow path pipe 18, and is supplied to the recovery vessel 7, in a state where a flow path on-off valve 18a for opening and closing the flow path of the liquid phase component outflow flow path pipe 18 is opened.

The recovery vessel 7 is a vessel for recovering the liquid phase component of the partial condenser 6 which is flowed out from the partial condenser 6 and flowed through the liquid phase component outflow flow path pipe 18 as a liquid purified product of propane (hereinafter referred to as "purified propane"), and storing the purified propane. The internal temperature of the recovery vessel 7 is maintained at a predetermined temperature by using the refrigerant circulator.

In addition, the recovery vessel 7 stores the liquid purified propane so that the gaseous phase is formed in a head space of the recovery vessel 7. A recovered gaseous phase component outflow flow path pipe 20 and a recovered gaseous phase component discharge flow path pipe 26 are connected to an upper portion on the gaseous phase side of the recovery vessel 7.

In a state where a flow path on-off valve 20a for opening and closing the flow path of the recovered gaseous phase component outflow flow path pipe 20 is opened, the gaseous phase component flowed out from the recovery vessel 7 flows through the recovered gaseous phase component outflow flow path pipe 20, and is returned to the partial condenser 6.

In addition, the gaseous phase component separated into the gaseous phase in the recovery vessel 7 flows through the recovered gaseous phase component discharge flow path pipe 26, and is discharged to the outside, in a state where a flow path on-off valve 26a for opening and closing the flow path of the recovered gaseous phase component discharge flow path pipe 26 is opened.

In addition, a purified propane outflow flow path pipe 23 is connected to a lower portion on the liquid phase side of the recovery vessel 7, and in a state where a flow path on-off valve 23a for opening and closing the flow path of the purified propane outflow flow path pipe 23 is opened, the liquid purified propane stored in the recovery vessel 7 flows through the purified propane outflow flow path pipe 23, and is supplied into the filling cylinder 8. The filling cylinder 8 stores the purified propane under pressure.

According to the propane production apparatus 100 of the embodiment and the propane production method performed by the propane production apparatus 100, in the hydrogenation reaction tower 3, the crude propylene and hydrogen are subjected to the hydrogenation reaction in the presence of the catalyst, so that the gaseous crude propane containing impurities is obtained.

In the case of generating propane by the hydrogenation reaction, since when the reaction temperature of the hydrogenation reaction accompanied by heat generation is excessively high, the impurities such as methane and ethane are generated, complicated temperature control of controlling the reaction temperature with high accuracy is required to obtain propane of high purity. A method for producing propane of high purity by using a hydrogenation reaction in which such a reaction temperature is controlled with high accuracy is not an efficient method.

Therefore, the propane production apparatus 100 of the embodiment does not control the reaction temperature of the hydrogenation reaction with high accuracy, but removes the impurities (main impurities include at least one of hydrogen, oxygen, nitrogen, water, methane, ethane, and propylene) contained in the crude propane obtained in the hydrogenation reaction tower 3 to obtain the purified propane of high purity in the first adsorption tower 4, the second adsorption tower 5, and the partial condenser 6. Accordingly, the propane production apparatus 100 of the embodiment can efficiently obtain the purified propane of high purity with high yield.

In addition, according to the propane production apparatus 100 of the embodiment, the first adsorption tower 4 and the second adsorption tower 5 adsorb and remove water, ethane, and propylene contained as impurities in the crude propane by an adsorption treatment in which the crude propane is brought into contact with the adsorbent (preferably, molecular sieve zeolite and molecular sieve activated carbon which are porous bodies having pores with pore diameters of 4 angstroms).

The primary purified propane after the adsorption treatment in the first adsorption tower 4 and the second adsorption tower 5 is subjected to partial condensation so that the partial condenser 6 separates and removes hydrogen, oxygen, nitrogen and methane contained as impurities in the primary purified propane. In this manner, hydrogen, oxygen, nitrogen, water, methane, ethane, and propylene contained as impurities in the crude propane obtained in the hydrogenation reaction tower 3 can be efficiently removed, and the purified propane of high purity (purity of 99.999 vol. % or more) can be obtained.

Figure 3:
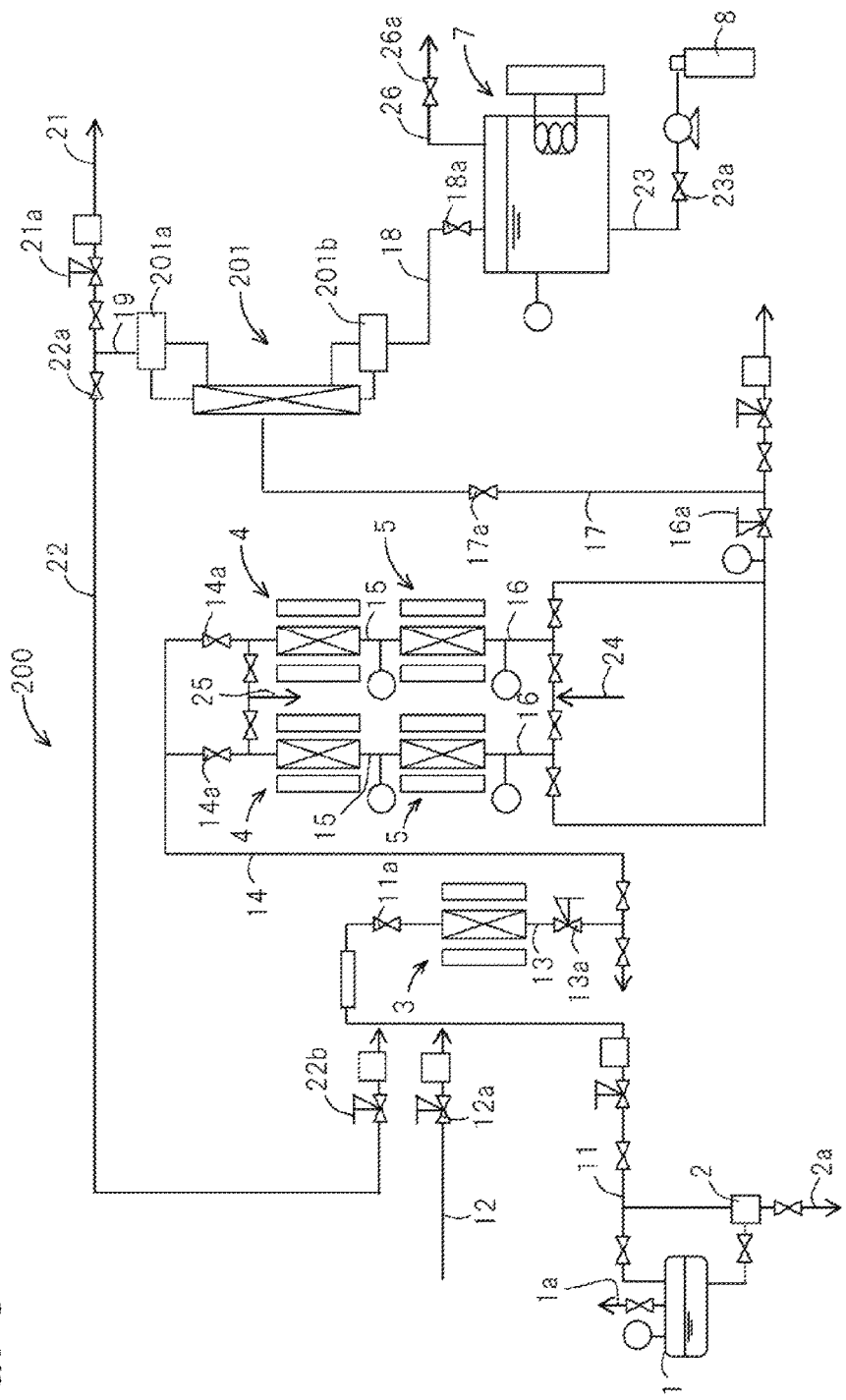
FIG. 3 is a diagram illustrating a configuration of a propane production apparatus 200 according to a second embodiment of the invention.

FIG. 3 is a diagram illustrating a configuration of a propane production apparatus 200 according to a second embodiment of the invention. The propane production apparatus 200 of the embodiment is similar to the propane production apparatus 100 described above, and corresponding parts will be denoted by the same reference numerals, and the description thereof will be omitted. The propane production apparatus 200 includes a distillation tower 201 in place of the partial condenser 6 provided in the propane production apparatus 100 described above. The propane production apparatus 200 is configured in the same manner as in the propane production apparatus 100, except for including the distillation tower 201.

The primary purified propane after the adsorption treatment in the first adsorption tower 4 and the second adsorption tower 5 is distilled so that the distillation tower 201 separates and removes hydrogen, oxygen, nitrogen and methane contained as impurities in the primary purified propane.

The distillation tower 201 forms a bottom space portion, a lower distillation portion, a central space portion, an upper distillation portion, and an upper space portion in order from the bottom, a heating device 201b is installed in the bottom space portion, and a condenser 201a is installed in the upper space portion. A heating medium such as heating water is supplied from the outside to the heating device 201b to support reboiling of the primary purified propane, and a refrigerant such as cooling water is supplied from the outside to the condenser 201a to support condensation of the primary purified propane.

In the central space portion of the distillation tower 201, the gaseous primary purified propane supplied from the second adsorption tower 5 via the primary purified propane supply flow path pipe 17 raises the upper distillation portion, and is rectified by gas-liquid contact with the reflux liquid flowing down. That is, the primary purified propane contained in the rising gaseous phase is dissolved and liquefied in the reflux liquid, and highly volatile hydrogen, oxygen, nitrogen and methane dissolved in the reflux liquid are vaporized. At this time, the purified propane of high purity purified by removing hydrogen, oxygen, nitrogen and methane which are highly volatile impurities flows down to the bottom space portion, and thereafter is discharged from the bottom space portion except for a part of the purified propane that is refluxed to the upper part of the upper distillation portion. On the other hand, hydrogen, oxygen, nitrogen, and methane which are highly volatile impurities, rise to the upper space portion to become concentrated gas, are subjected to cooling treatment by the condenser 201a, and continuously discharged as waste gas to the outside via the gaseous phase component discharge flow path pipe 21.

The distillation condition in the distillation tower 201 is not particularly limited, but, for example, the pressure in the first adsorption tower 4 and the second adsorption tower 5 is set to 0.3 MPaG. In a case where the primary purified propane after the adsorption treatment in the first adsorption tower 4 and the second adsorption tower 5 contains 9 vol. % of hydrogen as impurities, the distillation tower 201 is set under conditions of pressure of 0.2 MPaG, temperature of −25 to −15° C., reflux ratio of 0.5 to 2, and recovery rate of 90%. In order to obtain liquefied propane having a hydrogen impurity content concentration of 1 vol·ppm or less, the number of stages of the distillation tower 201 is approximately 3 to 6 stages (when tower height is approximately 3 m). The distillation condition of the above distillation tower 201 can be easily calculated based on the gas-liquid separation ratio.

The propane production apparatus 200 of the embodiment does not control the reaction temperature of the hydrogenation reaction with high accuracy, but removes the impurities (main impurities include at least one of hydrogen, oxygen, nitrogen, water, methane, ethane, and propylene) contained in the crude propane obtained in the hydrogenation reaction tower 3 to obtain the purified propane of high purity in the first adsorption tower 4, the second adsorption tower 5, and the distillation tower 201. Accordingly, the propane production apparatus 200 of the embodiment can efficiently obtain the purified propane of high purity with high yield.

Hereinafter, the invention will be described in more detail based on examples, but the invention is not limited to only these examples.

<Analysis of Impurity Content Concentration>

In the following examples and comparative examples, the propane purity and the concentrations of methane, ethane, propylene, isobutane, normal butane and pentane were analyzed using a gas chromatograph hydrogen flame ionization type detector (GC-FID), the concentrations of hydrogen, oxygen and nitrogen were analyzed using a gas chromatograph pulsed discharge photoionization detector (GC-PDD), and the concentration of water was analyzed using a capacitive dew point meter.

Example 1

Using the propane production apparatus 100 illustrated in FIG. 2, propane of high purity was produced under the following conditions. First, the liquid crude propylene was stored in the raw material propylene storage tank 1. In the liquid crude propylene, the impurity content concentration was 1.0 vol·ppm of methane, 100 vol·ppm of ethane, 4000 vol·ppm of propane, less than 1.0 vol·ppm of isobutane, less than 1.0 vol·ppm of normal butane, less than 1.0 vol·ppm of pentane, 200 vol·ppm of nitrogen, 5.0 vol·ppm of oxygen, and 2.0 vol·ppm of moisture.

In the liquid crude propylene, since the content concentrations of isobutane, normal butane, and pentane were less than 1.0 vol·ppm as described above, the total amount of liquid crude propylene flowed out from the raw material propylene storage tank 1 was vaporized in the vaporizer 2, and the vaporized gaseous crude propylene was flowed into the hydrogenation reaction tower 3. The hydrogenation reaction tower 3 was a cylindrical tube filled with a Pd/Al$_2$O$_3$ catalyst and having an inner diameter of 34 mm and a height of 400 mm. Specifically, a catalyst in which the Pd (0.5% by weight)/Al$_2$O$_3$ catalyst (N1182AZ, manufactured by JGC Catalysts and Chemicals Ltd, 3.0 mm diameter, and spherical shape) was diluted to 1% by weight with alumina balls (3.0 mm diameter and spherical shape) was used as the Pd/Al$_2$O$_3$ catalyst.

The hydrogenation reaction tower 3 was maintained at room temperature (25° C.) and a pressure of 0.33 MPaG, and a mixed gas (hydrogen/crude propylene=1.1/1) of gaseous crude propylene of 1.0 L/min and hydrogen (purity 99.999 vol. %) of 1.1 L/min was passed through the hydrogenation reaction tower 3. In the hydrogenation reaction tower 3, the heating temperature during the hydrogenation reaction was approximately 140° C., most of propylene in the crude propylene was hydrogenated to be propane, and the flow rate of the gaseous crude propane flowed out from the bottom portion of the hydrogenation reaction tower 3 was 1.1 L/min. Here, in the gaseous crude propane flowed out from the bottom portion of the hydrogenation reaction tower 3, the impurity content concentration was 11 vol·ppm of methane, 93 vol·ppm of ethane, 6.0 vol·ppm of propylene, less than 1.0 vol·ppm of isobutane, less than 1.0 vol·ppm of normal butane, less than 1.0 vol·ppm of pentane, 9.0 vol. % of hydrogen, 182 vol·ppm of nitrogen, less than 1.0 vol·ppm of oxygen, and 11.0 vol·ppm of moisture. It is considered that propane or propylene decomposes due to heat generation during the hydrogenation reaction in the hydrogenation reaction tower 3, methane and ethane increase more than the stoichiometric amounts, and moisture increases due to the reaction between oxygen and hydrogen. In addition, it is considered that propylene is remained as 6.0 vol·ppm unreacted.

The gaseous crude propane obtained by the hydrogenation reaction in the hydrogenation reaction tower 3 flows into the first adsorption tower 4 and the second adsorption tower 5. The first adsorption tower 4 was a cylindrical tube filled with molecular sieve activated carbon and having an inner diameter of 95.6 mm and a height of 1930 mm. Specifically, a 4A type porous body (CMS-4A-B, manufactured by Japan Enviro Chemicals Ltd) having a granular shape with a diameter of 2.3 mm and pores with a pore diameter of 4 angstroms was used as the molecular sieve activated carbon. In addition, the second adsorption tower 5 was a cylindrical tube filled with molecular sieve zeolite and having an inner diameter of 42.6 mm and a height of 1,500 mm. Specifically, a 4A type porous body (MS-4A, manufactured by Tosoh Corporation) having a granular shape with a diameter of 3.0 mm and pores with a pore diameter of 4 angstroms was used as the molecular sieve zeolite.

The gaseous crude propane was passed through the first adsorption tower 4 and the second adsorption tower 5, and helium gas as a regeneration gas was purged and substituted with propane. The end point of substitution was set to the helium concentration of 5 vol. % or less by gas chromatography (TCD analysis). The pressures of the first adsorption tower 4 and the second adsorption tower 5 were maintained at 0.3 MPaG. The time required for accumulating pressure up to the adsorption pressure was 130 minutes. In addition, the temperatures of the first adsorption tower 4 and the second adsorption tower 5 were maintained at 25° C. In this manner, after substitution with propane, the adsorption treatments in the first adsorption tower 4 and the second adsorption tower 5 were started. In the first adsorption tower 4, adsorption and removal of ethane and propylene in the crude propane are mainly performed, and in the second adsorption tower 5, adsorption and removal of the moisture in the crude propane are mainly performed.

In the gaseous primary purified propane flowed out from the bottom portion of the second adsorption tower 5 after the adsorption treatment in the first adsorption tower 4 and the second adsorption tower 5, the impurity content concentration was 11 vol·ppm of methane, less than 1.0 vol·ppm of ethane, less than 1.0 vol·ppm of propylene, less than 1.0 vol·ppm of isobutane, less than 1.0 vol·ppm of normal butane, less than 1.0 vol·ppm of pentane, 9.0 vol. % of hydrogen, 182 vol·ppm of nitrogen, less than 1.0 vol·ppm of oxygen, and less than 1.0 vol·ppm of moisture, and a removal of ethane and propylene was confirmed.

The gaseous primary purified propane flowed out from the bottom portion of the second adsorption tower 5 flows into the partial condenser 6 and is subjected to partial condensation, and thereafter the liquid purified propane flows into the recovery vessel 7. At this time, the pressure in a propane condensation region of the partial condenser 6 was set to 0.1 MPaG, the discharge flow rate of the gaseous phase component in the partial condenser 6 discharged from the gaseous phase component discharge flow path pipe 21 was set to 0.2 L/min, and the temperature of the recovery vessel 7 was set to −30° C. In addition, the total time of the treatment time of the adsorption treatment in the first adsorption tower 4 and the second adsorption tower 5 described above and the treatment time of the partial condensation treatment in the partial condenser 6 was set to 1000 minutes. After the partial condensation treatment in the partial condenser 6, the partial condenser 6 and the recovery vessel 7 were sealed.

The hydrogenation reaction in the hydrogenation reaction tower 3, the adsorption treatment in the first adsorption tower 4 and the second adsorption tower 5, and the partial condensation treatment in the partial condenser 6 as described above were repeated eight times in total, and 7200 L of purified propane in terms of gas was stored in the recovery vessel 7.

Next, the communication state between the partial condenser 6 and the recovery vessel 7 was established, the discharge flow rate of the gaseous phase component in the partial condenser 6 discharged from the gaseous phase component discharge flow path pipe 21 was set to 1.0 L/min, and an operation of discharging the gaseous phase component in the partial condenser 6 to the outside was performed. The operation of discharging the gaseous phase component in the partial condenser 6 to the outside was performed for 420 minutes.

In the purified propane recovered in the recovery vessel 7 as described above, the impurity content concentration was less than 1.0 vol·ppm of methane, less than 1.0 vol·ppm of ethane, less than 1.0 vol·ppm of propylene, less than 1.0 vol·ppm of isobutane, less than 1.0 vol·ppm of normal butane, less than 1.0 vol·ppm of pentane, less than 1.0 vol·ppm of hydrogen, less than 1.0 vol·ppm of nitrogen, less than 1.0 vol·ppm of oxygen, and less than 1.0 vol·ppm of moisture, and the purified propane of high purity, having a purity of 99.999 vol. % or more, was obtained. In this case, the obtained amount of purified propane was 6780 L in terms of gas and 13.3 kg in terms of weight. The yield at this time was 75 vol. % (Yield={6780 L/((130 L+1000 L)×8)}×100).

Example 2

Industrial propylene (purity 99.5%, manufactured by Mitsui Chemicals, Inc.) was supplied to a propylene purification section using a silver nitrate aqueous solution as an absorption liquid, and purified. Specifically, a cylindrical tube made of stainless steel (inner diameter of 54.9 mm×height 500 mm, volume of 1185 mL) was respectively used as an absorption tower and a stripping tower composed of a bubble tower. In the absorption tower, 735 mL (liquid level height of absorption liquid 310 mm) of 5 mol/L silver nitrate aqueous solution was stored, and in the stripping tower, 355 mL (liquid level height of absorption liquid 150 mm) of the same concentration of silver nitrate aqueous solution was stored.

As the conditions in the absorption tower, the internal pressure was 0.5 MPaG and the internal temperature was 25° C. As the conditions in the stripping tower, the internal pressure was 0.1 MPaG and the internal temperature was 25° C. The silver nitrate aqueous solution stored in the absorption tower and the stripping tower was circulated so that the flow rate is 25 mL/min. In the stripping tower, a stripping gas (purified propylene gas) was derived at 637 mL/min, the recovery rate was 96.1 mol %, and the purity was 99.99 mol %. In addition, in the absorption tower, non-absorbed gas was discharged at 26 mL/min and the discharge rate was 3.9 mol %.

The purified propylene of high purity obtained in this manner was used as the raw material propylene to be supplied to the hydrogenation reaction tower 3.

The hydrogenation reaction tower 3 was a cylindrical tube which was filled with the Pd (0.5% by weight)/$Al_2O_3$ catalyst (N1182AZ, manufactured by JGC Catalysts and Chemicals Ltd, 3.0 mm diameter, and spherical shape) diluted to 15% by weight with alumina balls (3.0 mm diameter and spherical shape), and having an inner diameter of 34 mm and a height of 550 mm. To the hydrogenation reaction tower 3, the raw material propylene gas (Purity 99.99 mol %) purified as described above was supplied at a flow rate of 0.8 L/min (indicating a value converted into flow rate at NTP, 0° C., and 1 atm), and the raw material hydrogen gas (EG grade, purity 99.9999 mol %, manufactured by Sumitomo Seika Chemicals Co., Ltd.) was supplied at a flow rate of 1.2 L/min (NTP). The molar ratio of each gas in the hydrogenation reaction tower 3 was propylene/hydrogen=2/3 (=1/1.5). As the hydrogenation reaction condition in the hydrogenation reaction tower 3, the internal pressure was set to 0.3 MPaG. At this time, the reaction temperature during the hydrogenation reaction in the hydrogenation reaction tower 3 increased to 350° C.

The gaseous crude propane flowed out from the bottom portion of the hydrogenation reaction tower 3 was flowed into the first adsorption tower 4 and the second adsorption tower 5 configured in the same manner as in Example 1, and thereafter, the purified propane was recovered in the recovery vessel 7 via the partial condenser 6 configured in the same manner as in Example 1. In the purified propane recovered in the recovery vessel 7 as described above, the impurity content concentration was less than 1.0 vol·ppm of methane, less than 1.0 vol·ppm of ethane, less than 1.0 vol·ppm of propylene, less than 1.0 vol·ppm of isobutane, less than 1.0 vol·ppm of normal butane, less than 1.0 vol·ppm of pentane, less than 1.0 vol·ppm of hydrogen, less than 1.0 vol·ppm of nitrogen, less than 1.0 vol·ppm of oxygen, and less than 1.0 vol·ppm of moisture, and the purified propane of high purity, having a purity of 99.999 vol. % or more, was obtained.

Comparative Example 1

Without using the crude propane obtained by the hydrogenation reaction in the hydrogenation reaction tower 3, the crude propane having impurity content concentration of 2 vol·ppm of nitrogen, less than 0.1 vol·ppm of oxygen, 0.2 vol·ppm of carbon dioxide, 2 vol·ppm of moisture, 4595 vol·ppm of ethane, 3 vol·ppm of propylene, 484 vol·ppm of isobutane, and 15 vol·ppm of normal butane, was flowed into three adsorption towers connected in series.

The first adsorption tower was a cylindrical tube with an inner diameter of 42.6 mm and a height of 1500 mm, filled with the molecular sieve zeolite which was a 4A type porous body (MS-4A, manufactured by Tosoh Corporation) having a granular shape with a diameter of 3.0 mm and pores with a pore diameter of 4 angstroms. The second adsorption tower was a cylindrical tube with an inner diameter of 95.6 mm and a height of 1930 mm, filled with the molecular sieve activated carbon which was a 4A type porous body (CMS-4A-B, manufactured by Japan Enviro Chemicals Ltd) having a granular shape with a diameter of 2.3 mm and pores with a pore diameter of 4 angstroms. The third adsorption tower was a cylindrical tube with an inner diameter of 28.4 mm and a height of 1800 mm, filled with activated carbon γ which was coconut shell crushed coal (KURARAY COAL GG, manufactured by Kuraray Chemical Co., Ltd) having a particle size of 10 to 20 meshes.

The crude propane was passed through the first, second and third adsorption towers, and helium gas serving as a regeneration gas was purged and substituted with propane. The end point of substitution was set to the helium concentration of 1 vol. % or less by gas chromatography (TCD analysis). The pressures of the first, second and third adsorption towers were maintained at 0.5 MPaG. The time required for accumulating pressure up to the adsorption pressure was 252 minutes. In addition, the temperatures of the first, second and third adsorption towers were maintained at 25° C. In this manner, after substitution with propane, the adsorption treatments in the first, second and third adsorption towers were started.

The gaseous primary purified propane flowed out from the bottom portion of the first, second and third adsorption towers was flowed into the partial condenser and was subjected to partial condensation, and thereafter the liquid purified propane was flowed into the recovery vessel. At this time, the pressure in a propane condensation region of the partial condenser was set to 0.1 MPaG, the discharge flow rate of the gaseous phase component in the partial condenser discharged from the gaseous phase component discharge flow path pipe was set to 0.15 L/min, and the temperature of the recovery vessel was set to −30° C. In addition, the total time of the treatment time of the adsorption treatment in the first, second and third adsorption towers described above and the treatment time of the partial condensation treatment in the partial condenser was set to 195 minutes.

In the purified propane recovered in the recovery vessel as described above, the impurity content concentration was less than 1.0 vol·ppm of methane, less than 1.0 vol·ppm of ethane, less than 1.0 vol·ppm of propylene, less than 1.0 vol·ppm of isobutane, less than 1.0 vol·ppm of normal butane, less than 1.0 vol·ppm of pentane, less than 1.0 vol·ppm of hydrogen, less than 1.0 vol·ppm of nitrogen, less than 1.0 vol·ppm of oxygen, and less than 1.0 vol·ppm of moisture, and the purified propane of high purity, having a purity of 99.999 vol. % or more, was obtained. The yield of purified propane in this case was 53.2 vol. %.

Comparative Example 2

Propane was generated by the hydrogenation reaction in the hydrogenation reaction tower 3 in the same manner as in Example 2 except that the first adsorption tower 4, the second adsorption tower 5 and the partial condenser 6 were not used. In Comparative Example 2, in propane generated by the hydrogenation reaction in the hydrogenation reaction tower 3, the impurity content concentration was 900 vol·ppm of methane and 650 vol·ppm of ethane, so that propane of high purity, having a purity of 99.999 vol. % or more, could not be obtained.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

REFERENCE SIGNS LIST

1: Raw material propylene storage tank
1a: Tank purge flow path pipe
2: Vaporizer
2a: Vaporizer purge flow path pipe
3: Hydrogenation reaction tower
4: First adsorption tower
5: Second adsorption tower
6: Partial condenser
7: Recovery vessel
8: Filling cylinder
11: Raw material supply flow path pipe
11a: Flow path on-off valve
12: Hydrogen introduction flow path pipe
12a: Flow path on-off valve
13: Crude propane outflow flow path pipe
13a: Flow path on-off valve
14: Crude propane supply flow path pipe
14a: Flow path on-off valve
15: Flow path pipe
16: Primary purified propane outflow flow path pipe
16a: Flow path on-off valve
17: Primary purified propane supply flow path pipe
17a: Flow path on-off valve
18: Liquid phase component outflow flow path pipe
18a: Flow path on-off valve
19: Gaseous phase component outflow flow path pipe
19a: Flow path on-off valve
20: Recovered gaseous phase component outflow flow path pipe
20a: Flow path on-off valve
21: Gaseous phase component discharge flow path pipe
21a: Flow path on-off valve
22: Gaseous phase component supply flow path pipe
22a: Flow path on-off valve
22b: Flow path on-off valve
23: Purified propane outflow flow path pipe
23a: Flow path on-off valve 24: Regeneration gas supply flow path pipe
25: Regeneration gas discharge flow path pipe
26: Recovered gaseous phase component discharge flow path pipe
26a: Flow path on-off valve
100: Propane production apparatus
200: Propane production apparatus
201: Distillation tower
201a: Condenser
201b: Heating device

The invention claimed is:

1. A propane production method, comprising:
a hydrogenation reaction step of hydrogenation-reacting crude propylene having a propylene purity of 95 mol % or more and comprising less than 1.0 vol·ppm isobutene, less than 1.0 vol·ppm normal butene, and less than 1.0 vol·ppm pentane, and hydrogen in a presence of a catalyst under conditions comprising a pressure of 0.0 MPaG to 1.0 MPaG and a temperature of 50° C. to 200° C. to obtain gaseous crude propane containing impurities; and
an impurity removal step of removing the impurities contained in the gaseous crude propane obtained in the hydrogenation reaction step to obtain a purified propane,
wherein the impurities include hydrogen, oxygen, nitrogen, water, methane, ethane, and propylene,
wherein the impurity removal step includes
an adsorptive removal stage of adsorbing and removing water, ethane and propylene contained as impurities in the gaseous crude propane by adsorption treatment in which the gaseous crude propane is brought into contact with an adsorbent, and
a separation removal stage of separating and removing hydrogen, oxygen, nitrogen and methane contained as impurities in the crude propane after the adsorption treatment by partial condensation or distillation of crude propane after the adsorption treatment in the adsorptive removal stage, and
wherein the adsorption treatment in the adsorptive removal stage is performed under conditions comprising a pressure of 0.1 to 0.3 MPaG.

2. The propane production method according to claim 1, wherein the adsorbent is molecular sieve zeolite and molecular sieve activated carbon.

3. The propane production method according to claim 2, wherein the molecular sieve zeolite and the molecular sieve activated carbon are porous bodies having pores with a pore diameter of 4 angstroms.

4. The propane production method according to claim 1, wherein the adsorption treatment in the adsorptive removal stage is performed under a temperature range of 5 to 50° C.

* * * * *